United States Patent [19]
Alphin et al.

[11] 4,036,957
[45] July 19, 1977

[54] PHENOXY COMPOUNDS IN COMBINATIONS TO SUPPRESS GASTRIC BLEEDING IN ASPIRIN THERAPY

[75] Inventors: Reevis Stancil Alphin; John Wesley Ward, both of Richmond, Va.

[73] Assignee: A. H. Robins Company, Inc., Richmond, Va.

[21] Appl. No.: 633,044

[22] Filed: Nov. 18, 1975

[51] Int. Cl.² ............................................ A61K 31/625
[52] U.S. Cl. ..................................................... 424/232
[58] Field of Search ................................ 424/272, 232

[56] References Cited

PUBLICATIONS

Modell–Drugs in Current Use and New Drugs (1973) p. 80.

Primary Examiner—Stanley J. Friedman

[57] ABSTRACT

Novel pharmaceutical methods, combinations and compositions for reducing gastric bleeding during aspirin therapy for inflammation are disclosed. Compounds used in combination with aspirin are phenoxy- and substituted-phenoxy alcohols, carbamates, aminoalcohols, carbamoylalcohols, oxazolidinones, pyrrolidines, thiosemicarbazides and aminoalkylacetamides. The compounds act systemically to ameliorate gastric bleeding otherwise caused by aspirin.

3 Claims, 1 Drawing Figure

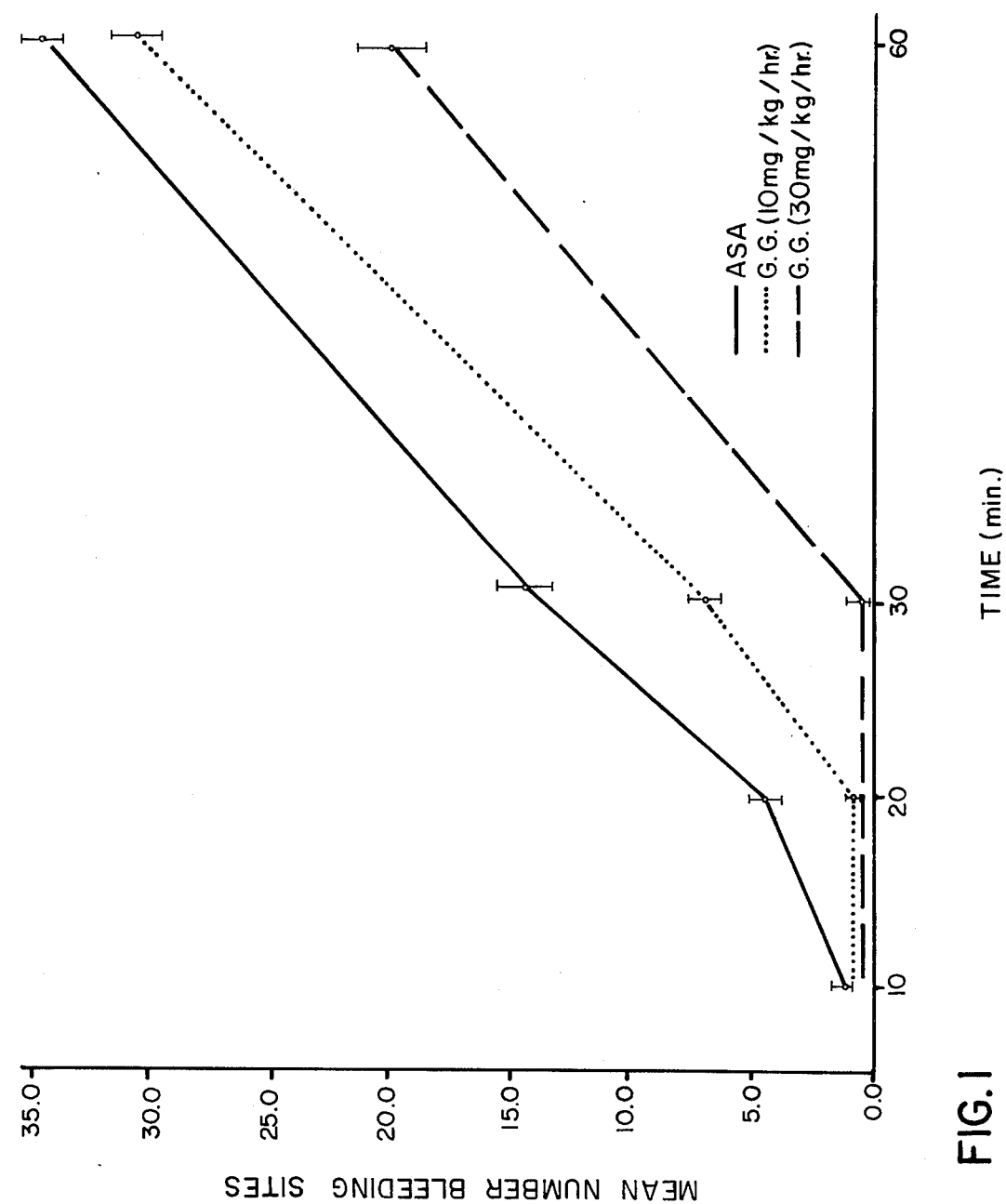

PHENOXY COMPOUNDS IN COMBINATIONS TO SUPPRESS GASTRIC BLEEDING IN ASPIRIN THERAPY

BACKGROUND OF THE INVENTION

The present invention relates to novel methods, combinations and compositions for reducing gastric bleeding during aspirin therapy in the treatment of inflammation. More particularly, the invention relates to methods, combinations and compositions therefor, of reducing gastric bleeding frequently fouund attendant to aspirin therapy in mammalian subjects which comprises administering in combination with aspirin, an effective amount of certain phenoxy compounds.

There are various diseases in chronic and acute form which afflict mammals and for which aspirin therapy is indicated and prescribed. In many instances high incidence of bleeding and ulceration results as side effects to the administration of aspirin for its anti-inflammatory effect. For example, high dosages of aspirin are administered to mammalian subjects in the treatment of inflammatory conditions associated with diseases generally described as rheumatic or arthritic types, but attendant to the beneficial effects of reduction of inflammation and swelling of joints and tissue in various parts of the mammalian body are detrimental effects of ulceration and bleeding with appreciable blood loss in the stomach. The need to overcome these side effects due to aspirin administration is well recognized in the fields of human and veterinary medicine and that in some cases the continual loss of blood cannot be tolerated. Oftentimes, aspirin therapy must be terminated, thus giving rise to exposure, in the search for other satisfactory chemotherapy, to the potential danger from certain other anti-inflammatory agents which may cause even more severe ulceration and perforation in certain parts of the gastro-intestinal tract. Thus, the accomplishment of the present invention in reducing bleeding due to aspirin therapy can be readily appreciated by one skilled in the art, particularly when it is realized that conditions of intolerance to aspirin because of induced ulceration and bleeding can be avoided by the methods, combinations and compositions of this invention.

Indicative of the state of the art have been attempts to find combinations which would allow administration of aspirin for its full therapeutic effect as an anti-inflammatory drug. Coprecipitates of aspirin with lignosulfonate (Brit. Pat. No. 1,345,358) with tannic acid (Brit. Pat. No. 1,345,359) and tea (Belg. Pat. No. 806,392) have all shown reduced irritation in the cat stomach.

Cyclobenzaprine combined with aspirin for muscle relaxing effect in aminals has been disclosed in British Pat. No. 1,334,326. The dosages of both cyclobenzaprine and aspirin are said to be subclinical and because less of these drugs are used, side effects are reduced. In the instant invention aspirin is administered in full dosage amount for its anti-inflammatory effect and the phenoxy compounds are coadministered to reduce the bleeding normally attendent to full dosage amounts of aspirin.

A composition of aspirin and 3-(o-methoxyphenoxy)-1,2-propanediol-1-carbamate, one of the compounds useful in this invention, is marketed by the A. H. Robins Company of Richmond, Virginia, as ROBAXISAL as a muscle relaxant-analgetic preparation. It contains these ingredients in a weight ratio of 1.22 of 3-(o-methoxyphenoxy)-1,2-propanediol-1-carbamate to 1 aspirin, which composition is outside the range of the present invention and contains from about two to about four times the 3-(o-methoxyphenoxy)-1,2-propanediol-1-carbamate useful for its optimum effect for the method of the present invention.

SUMMARY OF THE INVENTION

The present invention provides methods of treating mammals, including humans, for symptomatic conditions of inflammation for relief of which aspirin therapy is generally indicated but cannot be most effectively accomplished because of accompanying side effects due to gastric irritation caused by the aspirin. We have discovered that when certain phenoxy compounds are present systemically in the mammalian body during the period of time the mammalian stomach is exposed to aspirin following oral injestion of aspirin, bleeding and ulceration in the stomach is greatly reduced. The phenoxy or substituted phenoxy compounds capable of suppressing gastric bleeding caused by aspirin and useful in this invention are generally classed as phenoxyalcohols, carbamates, carbamoylalcohols, aminoalcohols, oxazolidinones, pyrrolidines, thiosemicarbazides and aminoalkylacetamides. In general, the method of this invention comprises administering daily normally effective amounts of from about 20 to about 200 mg/kg body weight aspirin in single or divided doses for the control of symptomatic conditions of inflammation and concomitantly administering from about 1 to about 100 mg/kg body weight of the phenoxy compounds of this invention in single or divided doses, said phenoxy compounds being administered at least during the time period aspirin is administered. The weight ratio of phenoxy compound to aspirin required for its intended effect does not exceed 0.5 to 1; i.e., 33% phenoxy compound, the effective required range being 0.05 to 0.5 parts by weight phenoxy compound per part by weight of aspirin. On the basis of 100 parts of the combination, phenoxy compound will therefore be from about 5 to 33 parts and the aspirin will be about 67 to 95 parts. In order to more effectively reduce or suppress initial bleeding caused by aspirin, the phenoxy compounds may be preadministered about 1 to 2 hrs. prior to the start of aspirin therapy to allow blood levels of the phenoxy compounds to build up to protective levels and thus prevent initial excess bleeding in senstive subjects. When the phenoxy compounds and aspirin are administered simultaneously but without preadministration, there will be an initial period of time before blood level of the phenoxy compounds has built sufficiently to give maximum protection against ulceration and bleeding; however, the bleeding will subside as blood levels build on continued use of the combination. The phenoxy compounds may be administered orally in physical combination with aspirin with or without adjuvants or carriers, or in separate dosage form from aspirin. In order to guard against neglect of administering the phenoxy compounds, the surest protection is obtained using the physical combination and for this reason as well as for convenience, the invention is also concerned with compositions containing the combination. In general, the compositions contain the proportions of the combination suitable for control of bleeding and ulceration outlined above for combined dosage forms and will contain about 0.05 to about 0.5 parts by weight of phenoxy compounds per part of aspirin for effective remedial control of ulceration and bleeding in the mammalian stomach. These novel compositions can therefore contain a percentage basis of contained aspirin and phenoxy compounds of Formula I from about 5 to about 33% by weight of the phenoxy compounds of Formula I and from about 67 to about 95% aspirin. Preferably, the compositions contain on a weight percentage basis of aspirin and phenoxy compound about 5 to 25% phenoxy compound of Formula I and 75 to 95% aspirin. Generally, the choice of ratio will depend on the phenoxy compound chosen for a particular mammalian species.

The phenoxy compounds useful in combination in pre-therapy and co-therapy with aspirin for anti-inflammatory treatment of mammals including humans have the formula:

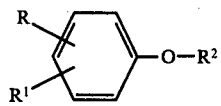

Formula I wherein;
R is selected from the group consisting of hydrogen, chlorine, bromine, fluorine, lower alkyl, lower alkoxy, or trifluoromethyl, $R^1$ is selected from the group consisting of hydrogen, chlorine, bromine, fluorine, lower alkyl, or lower alkoxy, and $R^2$ is selected from the group consisting of —CH(CH$_2$OH)$_2$, —CH$_2$CHOHCH$_2$OH, —CH$_2$CHOHCH$_2$OCONH$_2$, —CH$_2$CHOHCH$_2$OCONH-lower-alkyl, —CH$_2$CHOHCH$_2$OCON(lower-alkyl)$_2$, —CH$_2$CHOHCH$_3$, —CH$_2$CHOHCH$_2$NH-lower-alkyl, —CH$_2$CHOHCH$_2$NH(lower-alkyl)$_2$, —CH$_2$CHCH$_2$NHCOO, —CH$_2$CH(CH$_3$)OCONH$_2$, —CH$_2$CH(CH$_3$)OCONH-lower-alkyl, —CH$_2$CH(CH$_3$)OCON (lower-alkyl)$_2$, —CH$_2$OH(CH$_3$)OCONHCH(CH$_3$), —CH$_2$CHOHCH$_2$N(NH$_2$)  C(S)NHC$_2$H$_5$, —CHCH$_2$CH$_2$N(CONHCH$_3$)CH$_2$, —CH$_2$—CONHCH$_2$CH$_2$N(lower-alkyl)$_2$, or —CHCH$_2$CH$_2$N[CONHCH$_2$CH$_2$—N(CH$_3$)$_2$]CH$_2$.

The primary object of this invention is to provide a method of treating inflammation with aspirin in mammals, including humans, wherein the side effects of incidence of gastric bleeding and ulceration are greatly reduced in systemic action by administration of ulcer ameliorating compounds which are certain phenoxy compounds.

Another object of this invention is to provide a method of treating inflammation with aspirin; i.e., aspirin therapy, wherein the incidence of bleeding and ulceration are decreased by concomitant or co-administration of certain phenoxy compounds.

Another object of this invention is to provide a method of reducing intestinal ulceration due to aspirin therapy by preadministration of certain phenoxy compounds prior to co-administration of a combination of aspirin and said phenoxy compounds.

Another object of this invention is to provide pharmaceutical combinations of aspirin and certain phenoxy compounds in physical combination in unit dosage forms for co-administration which are useful for treating inflammation with reduced incidence of harmful bleeding and ulceration.

Another object of this invention is to provide protection by systemic means to the stomach of mammals against bleeding and ulceration caused by high doses of aspirin by administering the phenoxy compounds of this invention prior to and during the time of aspirin administration.

Still other objects will occur to one skilled in the art from the description which follows.

DETAILED DESCRIPTION OF THE INVENTION

According to the method of this invention which comprises combining the administration of phenoxy compounds of Formula I and aspirin in ratios on a 100 parts basis of about 5 to 33 parts of a phenoxy compound of Formula I and about 67 to 95 parts of aspirin, symptomatic relief of inflammation in mammals, including humans, is obtained with reduced side effects in the stomach.

Included among the phenoxy compounds of Formula I useful in the practice of this invention are:

| Compound No. | |
|---|---|
| 1 | 2-phenoxy-1,3-propanediol, |
| 2 | 3-phenoxy-1,2-propanediol, |
| 3 | 3-(o-methoxyphenoxy)-1,2-propanediol-1-carbamate, |
| 4 | N,N-dimethyl 3-(2-methoxyphenoxy)-1,2-propanediol-1-carbamate, |
| 5 | 1-(2-methoxyphenoxy)-2-propanol, |
| 6 | 1-(5-chloro-2-methoxyphenoxy)-2-propanol, |
| 7 | 3-(5-chloro-2-methoxyphenoxy)-1,2-propanediol, |
| 8 | 3-(2-methoxyphenoxy)-1,2-propanediol, |
| 9 | 3-(5-chloro-2-methylphenoxy)-1,2-propanediol-1-carbamate, |
| 10 | 1-(3-chloro-2-methylphenoxy)-2-propanol, |
| 11 | 3-(5-chloro-2-methylphenoxy)-1,2-propanediol, |
| 12 | 3-(5-chloro-2-methylphenoxy)-2-propanol, |
| 13 | 3-(5-chloro-2-methoxyphenoxy)-1,2-propanediol-1-carbamate, |
| 14 | 1-(n-butylamino)-3-(2-methoxyphenoxy)-2-propanol, |
| 15 | 5-(3,5-dimethylphenoxymethyl)-2-oxazolidinone, |
| 16 | 5-(2,4-dichlorophenoxymethyl)-2-oxazolidinone, |
| 17 | 1-(6-chloro-2-methylphenoxy)-2-propylcarbamate, |
| 18 | N-isopropyl 1-(4-chloro-2-methylphenoxy)-2-propylcarbamate, |
| 19 | 1-(3,5-dimethyl)-2-hydroxypropyl-4-ethyl thiosemicarbazide, |
| 20 | 3-(3-chlorophenoxy)-1-methylcarbamoyl-pyrrolidine, |
| 21 | 3-(4-chlorophenoxy)-2-hydroxypropylcarbamate, |
| 22 | 5-(2,6-dimethoxyphenoxymethyl)-2-oxazolidinone, |
| 23 | N-methyl-3-(2-methoxyphenoxy)-2-hydroxypropylcarbamate, |
| 24 | N,N-dimethyl-1-(4-chloro-2-methylphenoxy)-2-propylcarbamate, |
| 25 | 5-(2-methoxyphenoxymethyl)-2-oxazolidinone, |
| 26 | 3-(2-methylphenoxy)-1,2-propanediol, |
| 27 | 3-(2-methylphenoxy)-2-hydroxypropylcarbamate, |
| 28 | N-[2-(diethylamino)ethyl]-2-(p-methoxyphenoxyacetamide), |
| 29 | 1-carbamoyl-3-(3-trifluoromethylphenoxy)-pyrrolidine, and |
| 30 | 3-(3-chlorophenoxy)-N-[2-(dimethylaminoethyl) carboxamide]-1-pyrrolidine. |

The phenoxy compounds mentioned hereinabove are known. The carbamoyl, pyrrolidinyl, oxazolidinyl and amidoyl derivatives are disclosed in U.S. Pat. Nos. 2,976,213; 2,770,649; 3,062,827; 3,577,432; 2,895,960; 2,609,386 and Bull Soc. Chem. France 1960, 1786, or they can be prepared by methods disclosed in the aforesaid.

The term "lower alkyl" as used herein indicates straight and branched chain hydrocarbon radicals of up to four carbon atoms and is exemplified by such groups as methyl, ethyl, n-propyl, isopropyl, n-butyl, isobutyl and tertiarybutyl and the like. A "lower alkoxy" group has the formula —O-lower alkyl.

The term "phenoxy" as used herein indicates —O—phenyl and O-substituted phenyl wherein substitution is with groups R and R[1] as hereinabove defined.

EXAMPLES 1–21

The prevention of aspirin-induced bleeding in rats was determined by the following procedure. Female Sprague-Dawley rats weighing 150–180 g. were fasted for 24 hours on wire and divided into groups of six animals each. The rats were anesthetized and a ligature placed at the pyloric-duodenal junction. Groups serving as controls received normal saline (4.0 ml/kg, i.p.). The test compounds were administered at a dose of 100 mg/kg, i.p. to each of six animals 60 min. following pyloric ligation and 30 min. prior to aspirin administration (375 mg/kg, p.o.) in 2 ml. of artificial gastric juice (USP). Some of the compounds were tested at 50 mg/kg, i.p. The rats were sacrificed 60 min. after aspirin administration by cervical dislocation. The volume of the gastric contents was determined and compared against that produced with the same amount of aspirin for change in volume. Incidence and severity of gastric mucosal bleeding were also determined using an arbitrary grading system on a score of 0 to 40 by a pharmacologist who was unaware of the treatment schedule and results reported as the Gastric Bleeding Index. A score of zero would represent no mucosal hemorrhage and a score of 40 represents maximal hemorrhage seen in gastric mucosa of rats exposed to 375 mg/kg dose of aspiring for 60 min. (Gradation between 0 to 40 is on an even scale). The protective effect of the compounds of Formula I are summarized in Table 1. The data also show that reduction in bleeding is not necessarily dependent on reduction in gastric secretion.

EXAMPLE 22

Intraperitoneal Administration of Compound 15 of Table 1 In Rats

Compound 15 (metaxalone) which was very effective in preventing aspirin-induced gastric bleeding was evaluated over a range of dosage, i.p., in rats in the same procedure described above. The results are shown in Table 2.

Table 2

| | | | | | |
|---|---|---|---|---|---|
| \multicolumn{6}{c}{Effect of Metaxalone (Compound 15), i.p., on Aspirin-Induced Gastric Bleeding In Rats} | | | | | |
| Dose (mg/kg, i.p.) | Vol. Gastric Secretion (ml) | Total Hemoglobin Loss (mg) | Gastric Bleeding(1) Index | Percent Decrease in Mucosal Hemorrhage vs Control | P Value |
| Saline | 7.4 ± 0.4 | 34.0 ± 9.4 | 35.0 ± 4.1 | — | |
| 12.5 | 6.3 ± 0.3 | 19.3 ± 3.4 | 27.5 ± 4.2 | 21 | >.05 |
| 25.0 | 5.1 ± 0.3 | 15.3 ± 6.3 | 15.0 ± 5.0 | 57 | >.025 |
| 50.0 | 3.6 ± 0.5 | 2.5 ± 1.1 | 0.8 ± 0.8 | 98 | >.001 |
| 100.0 | 3.8 ± 0.4 | 2.5 ± 1.4 | 3.3 ± 1.7 | 91 | >.001 |

(1)$ED_{50}$ = 19.6 mg/kg.

EXAMPLES 23 and 24

Oral Administration of Compounds 3 and 15 of Table 1 in Dogs

Methocarbamol (Compound 3) and Metaxalone (Compound 15) were evaluated for their effectiveness upon oral administration against aspirin-induced gastric bleeding in dogs. Three female chronic Heindehain pouch dogs were used. Red blood cells from each dog were labeled with $Cr^{51}$. The dogs were fasted 24 hours Table 1

Effect of Phenoxy Compounds of Formula I on Aspirin-Induced Gastric Bleeding in Rats (a)

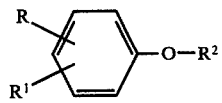

| Ex. (Compound No.) | R | R1 | R2 | Vol. % Decrease in Gastric Secretion | Gastric Bleeding Index | Percent Decrease in Mucosal Bleeding vs Control at 50 mg/kg | at 100 mg/kg |
|---|---|---|---|---|---|---|---|
| 1 | H | H | —CH(CH$_2$OH)2 | −8.7 | 31.7 | — | −15 |
| 2 | H | H | —CH$_2$CHOHCH$_2$OH | −14.1 | 20.0 | — | −14 |
| 3 | 2-CH$_3$O | H | —CH$_2$CHOHCH$_2$OCONH2 | −18.3 | 21.7 | — | −43 |
| 4 | 2-CH$_3$O | H | —CH$_2$CHOHCH$_2$OCONMe2 | −35.2 | 11.7 | — | −70 |
| 5 | 2-CH$_3$O | H | —CH$_2$CHOHCH3 | −42.0 | 12.5 | — | −66 |
| 6 | 2-CH$_3$O | 5-Cl | —CH$_2$CHOHCH3 | −42.2 | 1.7 | — | −93 |
| 7 | 2-CH$_3$O | 5-Cl | —CH$_2$CHOHCH$_2$OH | −42.0 | 19.2 | — | −49 |
| 8 | 2-CH$_3$O | H | —CH$_2$CHOHCH$_2$OH | −1.3 | 26.1 | −57 | −40 |
| 9 | 2-CH3 | 5-Cl | —CH$_2$CHOHCH$_2$OCONH2 | −36.6 | 7.2 | — | −81 |
| 10 | 2-CH3 | 3-Cl | —CH$_2$CHOHCH3 | −18.8 | 22.5 | — | −40 |
| 11 | 2-CH3 | 5-Cl | —CH$_2$CHOHCH$_2$OH | −29.7 | 20.8 | — | −10 |
| 12 | 2-CH3 | 5-Cl | —CH$_2$CHOHCH3 | −35.9 | 5.8 | — | −75 |
| 13 | 2-CH$_3$O | 5-Cl | —CH$_2$CHOHCH$_2$OCONH2 | −57.6 | 0.0 | — | −100 |
| 14 | 2-CH$_3$O | H | —CH$_2$CHOHCH$_2$NHC$_4$H9 | −35.6 | 5.8 | −78 | −70 (Toxic) |
| 15 | 3-CH3 | 5-CH3 | —CH$_2$CHCH$_2$NHCOO | −41.4 | 0.8 | −98 | −96 |
| 16 | 2-Cl | 4-Cl | —CH$_2$CHCH$_2$NHCOO | −44.6 | 0.0 | — | −100 |
| 17 | 2-CH3 | 6-Cl | —CH$_2$CH(CH$_3$)OCONH2 | −36.5 | 7.5 | — | −72 |
| 18 | 2-CH3 | 4-Cl | —CH$_2$CH(CH$_3$)OCONHCH(CH$_3$)2 | −29.3 | 19.2 | — | −28 |
| 19 | 3-CH3 | 5-CH3 | —CH$_2$CHOHCH$_2$N(NH$_2$)CSNHC$_2$H5 | −40.5 | 0.0 | — | −100 |
| 20 | 3-Cl | H | —CHCH$_2$CH$_2$N(CONHCH$_3$)CH$_2$ | −31.0 | 0.0 | — | −100 |
| 21 | 4-Cl | H | —CH$_2$CHOHCH$_2$OCONH2 | −30.5 | 4.2 | — | −78 |
| 30 | 3-Cl | H | —CHCH$_2$CH$_2$N[CONHCH$_2$CH$_2$—N(CH$_3$)$_2$]—CH$_2$ | −32.8 (b) | 0.8 (b) | −97 (b) | −100 |

(a) 6 rats each compound.
(b) at 30 mg/kg.

prior to any study and three days elapsed between studies. On experimental days each fundic pouch was rinsed with tepid tap water and then filled with 10 ml. of normal saline. After 30 minutes the saline was replaced with 10 ml. of artificial gastric juice (USP, pH 1.3). The dogs were given Compound 3 (200 mg/kg) or Compound 15 (50 and 100 mg/kg) or placebo (starch) orally in gelatin capsules. The 10 ml. of gastric juice was removed from the pouch after 60 minutes and replaced with another 10 ml. of juice containing 100 mg. of aspirin (80 mesh). This was likewise removed after 60 minutes. All samples collected from the pouches were counted for radio-activity using a deep-well counter. From the amount of radio-activity present in the gastric samples, the loss of blood into the pouch was determined. The results are shown in Table 3 and show the effectiveness of orally administering Compounds 3 and 15 in preventing aspirin-induced gastric bleeding.

i.v., of glyercyl guaiacolate there was no bleeding at 30 min. compared with an average of 14 bleeding sites when no glyceryl guaiacolate was adminsitered. A total of 23 cats were used and there was a minimum of 24 aspirin exposure sites for each dose of glyceryl guaiacolate.

EXAMPLE 26

Other Routes of Administration of Compound 8 in Rats

The effect of glyceryl guaiacolate (Compound 8) on aspirin-induced bleeding in rats was studied using the following procedure. Female Sprague-Dawley rats, weighing 140–160 g. and fasted for 24 hrs. on wire were divided into groups of 10 animals each. All animals were anesthetized with Metofane and a ligature placed at the pyloric-duodenal junction. Groups serving as controls received normal saline (4.0 ml/kg, i.p.). Some groups received normal saline and in addition were Table 3

Effect of Methocarbamol (Compound 3) and Metaxalone (Compound 15) on Aspirin-Induced Gastric Bleeding in CR[51] Labeled Heidenhain Pouch Dogs

| Protective Agent[1] | No. Expts. | Mucosal Blood Loss ($\mu$l) ± S.E. | | % Change from Control | P-Value | % Protection |
|---|---|---|---|---|---|---|
| | | Treatment | | | | |
| | | HCl | HCl + Aspirin | | | |
| None (starch) | 12 | 3.2 ± 0.5 | 17.0 ± 3.1 | +431 | <0.001 | — |
| Methocarbamol (200 mg/kg, p.o.) | 9 | 3.5 ± 0.7 | 6.6 ± 3.1 | +88 | > .05 | 79 |
| Metaxalone (50 mg/kg, p.o.) | 6 | 4.4 ± 2.4 | 8.6 ± 3.7 | +95 | >0.05 | 77 |
| Metaxalone (100 mg/kg, p.o.) | 6 | 13.0 ± 1.5 | 12.7 ± 3.5 | −2 | >0.05 | 100 |

[1]Protective agent or starch given orally 60 min. prior to aspirin administration.

EXAMPLE 25

Intravenous Administration of Compound 8 In Cats, Time Study

The effect of glyceryl guaiacolate (Compound 8) on aspirin-induced gastric bleeding in anesthetized cats was determined by the method of Alphin and Droppleman (J. Pharmaceut. Sci. 60: 1314, 1971). Fasted cats weighing 2.0–4.5 were anesthetized with phenobarbital sodium (130 mg/kg, i.p.). Glyceryl guaiacolate was administered intravenously for a total of 2 hrs. beginning 60 min. prior to the topical application of the aspirin (10 mg) to the gastric mucosa. Throughout the experiment, artificial gastric juice (USP, pH 1.3) bathed the mucosa by means of the specially designed chamber. The number of bleeding sites occurring at various exposure sites were recorded at 15, 30 and 60 min. Glyceryl guaiacolate was given at doses of 10 and 30 mg/kg/hr via a previously cannulated jugular vein using an infusion pump (Harvard Apparatus Co., Model 1202). The results are expressed as the mean number ± SE (standard error) of bleeding sites at the various time intervals in FIG. I which shows the number of bleeding sites with aspirin and glyceryl guaiacolate. It is evident that with increasig doses of glyceryl guaiacolate the gastric bleeding produced by aspirin was correspondingly reduced. An important point is that with 30 mg/kg/hr, given aspirin (375 mg/kg, p.o.) in artificial gastric juice; the remaining groups received aspirin in the same amount and also glyceryl guaiacolate 30 min. prior to the aspirin. The aspirin was administered in artificial gastric juice (USP, pH 1.1) in a total volume of 2 ml. to each rat. Following a recovery period of 1 hr. the animals received saline, aspirin and glyceryl guaiacolate in the amounts and by the routes indicated. In most of the experiments, 90 min. following aspirin the rats were sacrificed by cervical dislocation. The stomachs were removed and gastric contents collected for further analysis. The effects of glyceryl guaiacolate on aspirin-induced gastric bleeding in rats are depicted in Table 4. Hemoglobin loss produced by the aspirin was determined by the colorimetric method of Bing and Baker (J. Biol. Chem. 92: 589, 1931). The condition of the gastric mucosa was also assessed by determining the incidence and severity of damage using the scoring system described hereinabove to obtain the "Gastric Bleeding Index". It is evident from the data that aspirin-induced gastric irritation was markedly reduced when glyceryl guaiacolate was given at doses of 100 and 200 mg/kg by any route. The loss of blood into the gastric contents was also markedly reduced. There was a significant reduction in the volume of gastric secretion; however, a similar effect on pH was not observed.

Table 4

Effect of Glyceryl Guaiacolate (Compound 8) on Aspirin-Induced Bleeding in Rats

| Treatment In Addition to Saline, mg/kg (a) | | Volume Gastric Secretion | Total Hemoglobin Loss | Gastric Bleeding | Percent Decrease In Mucosal |
|---|---|---|---|---|---|
| Aspirin | Compound 8 | ml ± S.E. | mg ± S.E. | Index | Hemorrhage vs. Control |
| Series No. 1 Intraperitoneal (c) | | | | | |
| none | none | 6.8 ± 0.4 | 2.1 ± 0.3 | 1.5 ± 0.8 | — |
| ca 375 p.o. | none (control) | 7.9 ± 0.3 | 20.7 ± 4.5 | 28.5 ± 4.1 | — |

Table 4-continued

Effect of Glyceryl Guaiacolate (Compound 8) on Aspirin-Induced Bleeding in Rats

| Treatment In Addition to Saline, mg/kg (a) | | Volume Gastric Secretion ml ± S.E. | Total Hemoglobin Loss mg ± S.E. | Gastric Bleeding Index | Percent Decrease In Mucosal Hemorrhage vs. Control |
|---|---|---|---|---|---|
| Aspirin | Compound 8 | | | | |
| ca 375 p.o. | 100 i.p. | 4.2 ± 0.4 (b) | 8.2 ± 2.5 (b) | 6.5 ± 4.7 (b) | 77 (b) |
| Series No. 2 Intraperitoneal (c) | | | | | |
| none | none | 7.0 ± 0.4 | 2.6 ± 0.4 | 2.0 ± 0.4 | — |
| ca 375 p.o. | none (control) | 7.5 ± 0.3 | 27.8 ± 2.1 | 30.0 ± 2.6 | — |
| ca 375 p.o. | 50 i.p. | 6.4 ± 0.4 | 26.7 ± 3.1 | 26.0 ± 2.6 | 13.3 |
| ca 375 p.o. | 200 i.p. | 4.1 ± 0.4 (b) | 14.5 ± 3.9 (b) | 6.0 ± 2.1 (b) | 80.0 (b) |
| Series No. 3 Oral (d) | | | | | |
| ca 375 p.o. | none (control) | 7.1 ± 0.2 | 27.3 ± 3.2 | 35.5 ± 2.8 | — |
| ca 375 p.o. | 50 | 8.0 ± 0.3 | 29.4 ± 3.2 | 30.5 ± 2.4 | 14.2 |
| ca 375 p.o. | 100 | 6.5 ± 0.3 | 26.2 ± 4.6 | 21.0 ± 2.7 | 41.5 |
| ca 375 p.o. | 200 | 6.5 ± 0.5 | 20.2 ± 1.5 | 19.0 ± 3.9 (b) | 46.5 (d) |
| Series No. Intraduodenal (e) | | | | | |
| ca 375 p.o. | none (control) | 5.6 ± 0.9 | 21.2 ± 10.8 | 20.0 ± 3.3 | — |
| ca 375 p.o. | 50 | 5.0 ± 0.2 | 12.4 ± 2.3 | 18.0 ± 4.1 | 10.0 |
| ca 375 p.o. | 100 | 3.9 ± 0.2 (b) | 7.7 ± 1.2 (b) | 9.5 ± 2.5 (b) | 57.5 (b) |
| ca 375 p.o. | 200 | 3.5 ± 0.3 (b) | 4.4 ± 1.0 (b) | 2.0 ± 1.1 (b) | 90.0 (b) |

(a) Ten rats used in each test within a series.
(b) P-Value is <0.05 and result statistically significant.
(c) Compound 8 given i.p.
(d) Compound 8 given orally.
(e) Compound 8 given duodenally.

EXAMPLE 27

Other Routes of Administration of Compound 3 in Rats

Following the procedure of Example 26, methocarbamol (Compound 3) was tested further in rats via intraperitoneal and intraduodenal administration. Results are in Table 6. Methocarbamol was found to be significantly effective in reducing bleeding at a ratio of one part by weight methocarbamol to 3.75 parts aspirin.

EXAMPLE 28

Effect of Compound 15 on the Anti-Inflammatory Activity of Aspirin in Rats

The effect of metaxalone (Compound 15) on the antiinflammatory activity of aspirin in rats was studied using a modification of the Evans Blue-Carrageenan Pleural Effusion Test [Sancilio, L. F., Journal of Pharmacology and Experimental Therapeutics 168, 199–204 (1969)]. The results summarized in Table 5 show that 100 mg/kg of metaxalone administered 30 min. prior to administration of 150 mg aspirin/kg, p.o. and again 2 hrs. after injection of Carrageenan had no effect on the anti-inflammatory effectiveness of aspirin.

Table 5

Effect of Metaxalone (Compound 15) on the Anti-Inflammatory Activity of Aspirin in The Evans Blue-Carrageenan Pleural Effusion Assay in Rats

| Compound | Dose Aspirin mg/kg oral | Dose Metaxalone mg/kg oral | Pleural Fluid ml ± S.D. | % Decrease in Pleural Fluid vs Control | P-Value |
|---|---|---|---|---|---|
| Aspirin | 150 | 0 | 4.2 ± 0.28 | 38 | <0.05 |
| Aspirin + Metaxalone* | 150 | 200 | 4.3 ± 0.40 | 37 | <0.05 |
| Control (0.5% Tween 80 10 mg/kg) | 0 | 0 | 6.8 ± 0.64 | — | — |

*Metaxalone 100 mg. administered 30 minutes prior to aspirin; 100 mg. metaxalone administered 2 hours after injection of irritant.

METHODS OF ADMINISTRATION

Table 6

Effect of Methocarbamol (Compound 3) on Aspirin-Induced Bleeding In Rats

| Treatment In Addition to Saline, mg/kg (a) | | Volume Gastric Secretion ml ± S.E. | Total Hemoglobin Loss mg ± S.E. | Gastric Bleeding Index | Percent Decrease In Mucosal Hemorrhage vs. Control |
|---|---|---|---|---|---|
| Aspirin | Compound 3 | | | | |
| Series No. 1 Intraperitoneal (c) | | | | | |
| 375 | none | 6.3 ± 0.4 | 23.3 ± 3.4 | 34 ± 3 | — |
| 375 | 50 | 6.2 ± 0.5 | 22.4 ± 2.4 | 34 ± 2 | none |
| 375 | 100 | 5.5 ± 0.3 | 11.6 ± 3.6 (b) | 13 ± 6 (b) | 62 |
| 375 | 200 | 3.7 ± 0.4 (b) | 1.5 ± 0.5 (b) | 1 ± 1 (b) | 97 |
| Series No. 2 Intraduodenal (d) | | | | | |
| 375 | none | 6.3 ± 0.4 | 26.0 ± 1.3 | 33 ± 4 | — |
| 375 | 100 | 5.0 ± 0.1 (b) | 27.8 ± 0.1 (b) | 24 ± 3 | 27 |
| 375 | 200 | 3.5 ± 0.6 (b) | 7.0 ± 2.8 (b) | 11 ± 6 (b) | 67 |
| 375 | 400 | 1.3 ± 0.1 (b) | 5.1 ± 3.6 (b) | 0.4 ± 1 (b) | 99 |

(a) Six rats used in each test within a series. Aspirin given orally in 2 ml. artificial gastric juice.
(b) P-Value is <0.05 and result statistically significant.
(c) Compound 3 given i.p.; aspirin given p.o.
(d) Compound 3 given i.d.; aspirin given p.o.

The combination of aspirin and phenoxy compounds useful in this invention is administered to a variety of mammals including humans, dogs, cats and horses suffering from inflammatory symptoms associated with chronic and acute rheumatoid and degenerative joint disease and other manifestations such as bursitis. The greatest benefit from use of the combination of this invention is derived by administering the phenoxy compounds about 1-2 hours prior to the start of the administration of the combination and the protective, remedial and ameliorating effect of the phenoxy compounds is thus maximized. The combination may be given orally and simultaneously or separately. The phenoxy compounds may be given in injectable form prior to and during oral administration of aspirin. It is not necessary that the phenoxy compounds and aspirin be given at precisely the same time of the day, the important requisite being that nblood levels of the phenoxy compounds be sufficiently high to effectively combat the ulcerative effect of aspirin on the gastric tissue of the mammalian stomach. Generally, however, once the preadministration period for the phenoxy compound has passed, in order to insure that administration of the phenoxy compounds is not neglected, the surest procedure is to administer the combination orally in mixture such as, for example, powders, slurries or layered tablets; therefore, this procedure and a composition based on the combination represent preferred embodiments of the invention.

According to the present invention as disclosed hereinabove, it has been found that bleeding and ulceration of the stomach caused by aspirin therapy is minimized when the phenoxy compounds of Formula I are also administered in a ratio of in parts by weight of about 0.05 to about 0.5 parts per weight of aspirin. The ampount of aspirin contained in the combinations or compositions of this invention administered on a daily basis varies from about 20 to 200 mg/kg body weight. Thus, for example, on a daily basis subjects receiving the combination at the highest ratio of phenoxy compound to aspirin at its upper dosage range would receive on a daily basis 100 mg/kg phenoxy compound and 200 mg/kg aspirin. In general, the pretreatment with phenoxy compound about 1-2 hrs. prior to start of aspirin therapy may vary from about 10 to about 100 mg/kg body weight.

The choice of ratio within the range of about 0.05 to about 0.5 parts by weight phenoxy compound of Formula I per part of aspirin used in any combination or composition on a variety of subjects will depend somewhat on the species of chemical used. It will also depend on such factors as sensitivity of the subject to aspirin and to species of mammal under treatment.

When the combinations of this invention are administered as a composition the mixture will be in a form suitable for oral use, for example, as tablets, hard or soft capsules, aqueous or oily suspensions, dispersible powders or granules, emulsions, hard or soft capsules or syrups or elixirs. The compositions may be prepared according to any known method for the manufacture of pharmaceutical compositions and such compositions may contain one or more agents selected from sweetening agents, flavoring agents, preserving agents and coloring agents in order to provide a pharmaceutically elegant and palatable preparation. Tablet contain the active ingredient in admixture with non-toxic pharmaceutically acceptable excipients which are suitable for the manufacture of tablets. These excipients may be, for example, inert diluents such as lactose, calcium or sodium phosphate, calcium or sodium carbonate, granulating and disintegrating agents such as maize, starch or alginic acid and its salts; binding agents, for example, starch, gelatin or acacia and lubricating agents, for example, magnesium stearate, stearic acid or talc. The tablets may be coated by known techniques to delay disintegration and absorption in the gastrointestinal tract and thereby provide a sustained action over a longer period. For example, monostearate or glyceryl distearate or a waxy material may be inclosed in hard gelatin capsules mixed therewith with an inert solid diluent, for example, calcium carbonate, calcium phosphate, lactose, magnesium stearate or Kaolin, or in soft gelatin capsules which the active ingredient is mixed with a liquid carrier such as water or an oily medium, for example, vegetable oil, or mineral oil.

Aqueous suspensions containing the combinations with excipients suitable for the manufacture of aqueous suspensions may be used. Suitable excipients are suspending agents, for example, sodium carboxyethylcellulose, methylcellulose, hydroxypropylmethylcellulose, sodium alginite, polyvinylpyrrolidone, gum tragacouth and acacia. Dispersing agents included may be naturally occurring phosphatides such as lecithin, condensation products of an alkalene oxide with fatty acids, for example, polyoxyethylene stearate, condensation products of ethylene oxide with long chain alipheter alcohols, for example, heptadecoethyleneoxycetanol, condensation products of ethylene oxide with partial esters derived from fatty acids and a hexitol, for example, polyoxyethylene sorbits, mono oleate, or condensation products of ethylene oxide with partial esters derived from fatty acids and hexitol anhydrides, for example, polyoxyethylene sorbitan mono-oleate. The said aqueous suspension may also contain preservatives, for example, ethyl or n-propyl-p-hydroxybenzoate, coloring agents, flavoring agents, sweetening agents such as sucrose or saccharin.

Oily suspensions may be formulated by suspending the aspirin and the ulcer ameliorating agent, a phenoxy compound of Formula I in a vegetable oil, for example, a mineral oil, olive oil, coconut oil, or the like. The oily suspensions may contain a thickening agent such as wax or waxy alcohols. Flavoring and sweetening agents may be added to provide oral preparations which are palatable. Antioxidants such as ascorbic acid may be added as preservatives.

Dispersible powders and granules of anti-inflammatory agent and ameliorating agent suitable for preparation of oral dosage forms which are aqueous suspensions when water is added are provided when dispersing agents, suspending agents, and preservatives are admixed. Suitable dispersing agents and suspending agents are exemplified by those already mentioned above. Sweetening, flavoring and coloring agents may also be present.

Compositions containing the combinations of this invention may also be in the form of oil-in-water emulsions. The oily phase may be an edible oil such as the oils already described above for preparing oily suspensions. Suitable emulsifying agents may be naturally-occurring gums, for example, gum acacia or gum tragacanth, naturally-occurring phosphatides, for example, soy bean lecithin, and esters or partial esters derived from fatty acids and hexitol anhydrides, for example, sorbitan mono-oleate, and condensation products of the said partial esters with ethylene oxide, for example, polyoxyethylene sorbitan mono-oleate. The emulsions may also contain sweetening and flavoring agents.

Syrups and elixirs may be formulated with sweetening agents, for example, glycerol, sorbitol or sucrose. Such formulations may also contain a demulcent, a preservative and flavoring and coloring agents.

Alternately, according to the method of this invention, aspirin in any form whatsoever and a phenoxy compound of Formula I in any pharmaceutically suitable form whatsoever, such as tablets, capsules, suspensions, etc., may be administered concomitantly to a mammalian subject in need of treatment for inflammation for the purpose of ameliorating the undesirable side effects of aspirin and the phenoxy compound in any pharmaceutically suitable form whatsoever, such as tablets, suspensions, capsules may be administered preceding said concomitant treatment for ulcer and hemorrhagic ameliorating effects which would otherwise occur due to side effects of aspiring therapy. Solutions of phenoxy compound in dimethylisosorbide may be prepared as described in U.S. Pat. No. 3,699,230 or in polyethylene glycol as described in U.S. Pat. No. 2,976,213 and administered when separate administration is the choice.

For veterinary oral use, the combination of aspirin and phenoxy compounds of Formula I are conveniently prepared in tablets and capsules for unit dosage form of administration or in the form of powders and granules for admixing with food.

The tablets and capsules for veterinary use are generally prepared as described hereinabove and in the formulations to follow and will be commensurate in dosage size to the size of the animal.

The powders and granules for admixing with food suitable for animals are conveniently prepared as hereinabove described or in the form of a food premix. The food premix which can be quite dilute can comprise the combinations of this invention in admixture with edible pharmaceutical diluent such as starch, oatmeal, flour, calcium carbonate, talc, dried fish meal and dried meat meals. The powders of the prepared premix is then conveniently added to the regular feed, thereby providing the anti-inflammatory action of aspirin but without high incidence of bleeding and ulceration due to the ameliorating effects of the phenoxy compound during the course of feeding. Granules of the combination of this invention may be prepared and coated for better reception in food by certain mammals which exhibit "finicky" eating habits such as cats and dogs.

The term "unit dosage form" as used in the specification and claims refers to physically discrete units suitable as unitary dosages for human subjects and animals, each unit containing a predetermined combination of aspirin and the ulcer ameliorating phenoxy compound calculated to produce the desired therapeutic effect in association with the required pharmaceutical diluent, carrier or vehicle. The specifications for the novel preferred unit dosage forms wherein the said combination is used are dictated by and directly dependent on (a) the effective amount of aspirin required for control of given symptoms and the sensitivity of the subject to the aspirin in the requirement of amount of ameliorating agent needed as disclosed hereinabove, (b) the limitations inherent in the art of compounding such active combinations for therapeutic use in humans and animals as disclosed in detail in this specification, these being features of the present invention. Examples of suitable unit dosage forms in accord with this invention are tablets, capsules, pills, powder pockets, granules, segregated multiples of any of the foregoing including the aspirin and the phenoxy compound and other forms as herein described.

It will be understood, however, that the specific dose level for any particular patient will depend upon a variety of factors, including the activity of the aspirin in a given subject and the ameliorating effect of the phenoxy compound employed, the age, body weight, general health, sex, diet, mammalian specie, time of administration, and the severity of the particular disease undergoing therapy. In general, the dosage regimen in carrying out the methods of this invention is that which ensures maximum therapeutic response with maximum protection to the subject against side effects of the contained aspirin and thereafter is the minimum effective level which continues to provide relief. It will also be understood that while the combinations of the method of this invention are preferably prepared in unit dosage form containing both the ulcer ameliorating agent and the aspirin, the method of the invention also encompasses separate administration of these agents to subjects suffering from the symptomatic problems in subjects in need of aspirin therapy, particularly of arthritic type disease, in unit dosage form of said agents. The method also encompasses preadministration of the ulcer and hemorrhage ameliorating phenoxy compound at least 1 to 2 hr. prior to the period of beginning of administration of the aspirin be it in combined composition with the ulcer ameliorating compound of this invention or be it administered separately but concomitantly with said ameliorating compound.

The compositions of this invention which are used in the co-administration of both aspirin and phenoxy compounds in the same unit dosage form suitable for human use but which may also be suitable for animals in these proportions are illustrated by the following examples for human administration which are not intended to be limiting within the scope of the invention in any way.

FORMULATIONS

Example 1-F (1) Capsules

Typical formulations for encapsulation are:

(a)

| | Per capsule, mg. |
|---|---|
| Aspirin | 325 |
| Metaxalone | 75 |
| Lactose | 200 |
| Starch | 2 |
| | 612 Total |

(b)

| | |
|---|---|
| Aspirin | 325 |
| Glyceryl guaiacolate | 150 |
| Lactose | 150 |
| Magnesium stearate | 2 |
| | 627 Total |

Example 2-F (2) Tablets

Typical formulations for tableting are:

| | Per tablet, mg. |
|---|---|
| Aspirin | 325 |
| Metaxalone | 100 |
| Alginic acid | 20 |
| Calcium and ammonium alginate | 40 |
| Starch | 50 |
| Lactose | 60 |
| Magnesium stearate | 2 |
| | 597 Total |

The compounds are thoroughly blended and tableted.

Example 3-F (3) Suspensions

A typical formulation for suspensions is:

| | |
|---|---|
| Aspirin | 375 |
| Metaxalone | 100 |

Example 3-F-continued (3) Suspensions

A typical formulation for suspensions is:
| | |
|---|---|
| Polysorbate | .1 |
| Methylester of parahydroxybenzoate | 0.3 |
| Sodium chloride | 1.0 |
| Distilled water | 523.6 |
| | 1000.0  Total |

All components except water are finely divided to less than 200 mesh size and shaken with the water prior to the time of use.

What is claimed is:

1. The method of treating inflammatory conditions in mammals which comprises administering to said mammals an effective amount of a combination of from about 67 to 95% by weight aspirin and from about 5 to 33% by weight of a phenoxy compound having the formula:

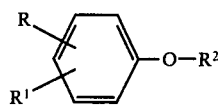

wherein;

R is selected from the group consisting of hydrogen, chlorine, bromine, fluorine, lower-alkyl, lower-alkoxy, or trifluoromethyl, $R^1$ is selected from the gruup consisting of hydrogen, chlorine, bromine, fluorine, lower-alkyl or lower-alkoxy, and $R^2$ is $-CH_2-CHCH_2NHCOO$.

2. The method of claim 1 wherein the phenoxy compound is 5-(3,5-dimethylphenoxymethyl)-2-oxazolidinone.

3. The method of claim 1 wherein the phenoxy compound is 5-(2,4-dichlorphenoxymethyl)-2-oxazolidinone.

* * * * * page 1 of 2 pages

UNITED STATES PATENT AND TRADEMARK OFFICE
CERTIFICATE OF CORRECTION

PATENT NO. : 4,036,957
DATED : July 19, 1977
INVENTOR(S) : Reevis Stancil Alphin and John Wesley Ward It is certified that error appears in the above-identified patent and that said Letters Patent are hereby corrected as shown below:

Col. 5, that portion of Table 1 contained therein should read as follows instead of as in the patent.

| Ex. (Compound No.) | R | $R^1$ | $R^2$ |
|---|---|---|---|
| 1 | H | H | $-CH(CH_2OH)_2$ |
| 2 | H | H | $-CH_2CHOHCH_2OH$ |
| 3 | $2-CH_3O$ | H | $-CH_2CHOHCH_2OCONH_2$ |
| 4 | $2-CH_3O$ | H | $-CH_2CHOHCH_2OCONMe_2$ |
| 5 | $2-CH_3O$ | H | $-CH_2CHOHCH_3$ |
| 6 | $2-CH_3O$ | $5-Cl$ | $-CH_2CHOHCH_3$ |
| 7 | $2-CH_3O$ | $5-Cl$ | $-CH_2CHOHCH_2OH$ |
| 8 | $2-CH_3O$ | H | $-CH_2CHOHCH_2OH$ |
| 9 | $2-CH_3$ | $5-Cl$ | $-CH_2CHOHCH_2OCONH_2$ |
| 10 | $2-CH_3$ | $3-Cl$ | $-CH_2CHOHCH_3$ |
| 11 | $2-CH_3$ | $5-Cl$ | $-CH_2CHOHCH_2OH$ |
| 12 | $2-CH_3$ | $5-Cl$ | $-CH_2CHOHCH_3$ |
| 13 | $2-CH_3O$ | $5-Cl$ | $-CH_2CHOHCH_2OCONH_2$ |
| 14 | $2-CH_3O$ | H | $-CH_2CHOHCH_2NHC_4H_9$ |
| 15 | $3-CH_3$ | $5-CH_3$ | $-CH_2\underline{CHCH_2NHCO}$ |
| 16 | $2-Cl$ | $4-Cl$ | $-CH_2\underline{CHCH_2NHCO}$ |
| 17 | $2-CH_3$ | $6-Cl$ | $-CH_2CH(CH_3)OCONH_2$ |
| 18 | $2-CH_3$ | $4-Cl$ | $-CH_2CH(CH_3)OCONHCH(CH_3)_2$ |
| 19 | $3-CH_3$ | $5-CH_3$ | $-CH_2CHOHCH_2N(NH_2)CSNHC_2H_5$ |
| 20 | $3-Cl$ | H | $-\underline{CHCH_2CH_2N(CONHCH_3)CH_2}$ |
| 21 | $4-Cl$ | H | $-CH_2CHOHCH_2OCONH_2$ |
| 30 | $3-Cl$ | H | $-\underline{CHCH_2CH_2N[CONHCH_2-N(CH_3)_2]-CH_2}$ |

UNITED STATES PATENT AND TRADEMARK OFFICE
CERTIFICATE OF CORRECTION

PATENT NO. : 4,036,957
DATED : July 19, 1977
INVENTOR(S) : Reevis Stancil Alphin and John Wesley Ward It is certified that error appears in the above-identified patent and that said Letters Patent are hereby corrected as shown below:

Col. 5, line 30, change "aspiring" to read --aspirin--

Col. 7, line 58, change "increasig" to read --increasing--

Col. 16, line 12, change "gruup" to read --group--

Col. 16, line 15, should read --$R^2$ is $-CH_2-\underline{CHCH_2-NHCOO}$-- instead of as in the patent.

Col. 6, last column in Table 2, change P Values " >.025 >.001, and >.001" to read -- <.025, <.001, and <.001-- respectively.

Signed and Sealed this

Twenty-first Day of March 1978

[SEAL]

Attest:

RUTH C. MASON
Attesting Officer

LUTRELLE F. PARKER
Acting Commissioner of Patents and Trademarks